(12) United States Patent
Evans et al.

(10) Patent No.: US 12,702,517 B2
(45) Date of Patent: Aug. 11, 2026

(54) QUICK RELEASE TOURNIQUET CARRIER

(71) Applicant: Edge-Works Manufacturing Company, Burgaw, NC (US)

(72) Inventors: Scott V. Evans, Burgaw, NC (US); Nicholas R. Tomczak, Richlands, NC (US)

( * ) Notice: Subject to any disclaimer, the term of this patent is extended or adjusted under 35 U.S.C. 154(b) by 0 days.

(21) Appl. No.: 18/817,524

(22) Filed: Aug. 28, 2024

(65) Prior Publication Data

US 2024/0415597 A1 Dec. 19, 2024

Related U.S. Application Data

(63) Continuation of application No. 17/929,292, filed on Sep. 1, 2022, now abandoned.

(60) Provisional application No. 63/239,527, filed on Sep. 1, 2021.

(51) Int. Cl.

| | |
|---|---|
| ***A61B 50/31*** | (2016.01) |
| ***A61B 17/132*** | (2006.01) |
| ***B65D 25/10*** | (2006.01) |
| ***B65D 43/02*** | (2006.01) |
| ***B65D 43/22*** | (2006.01) |
| *A61B 50/00* | (2016.01) |
| *A61B 50/30* | (2016.01) |

(52) U.S. Cl.

CPC .......... *A61B 50/31* (2016.02); *A61B 17/1325* (2013.01); *B65D 25/108* (2013.01); *B65D 43/0206* (2013.01); *B65D 43/22* (2013.01); *A61B 2050/0082* (2016.02); *A61B 2050/0083* (2016.02); *A61B 2050/3013* (2016.02); *A61B 2050/311* (2016.02)

(58) Field of Classification Search

CPC . A61B 50/31; A61B 2050/311; B65D 25/108; B65D 25/005; B65D 25/102; B65D 43/0206; B65D 43/02; B65D 45/16; B65D 5/643; A45C 13/30

USPC ....... 206/210, 211, 570, 440, 83.5, 451, 676

See application file for complete search history.

(56) References Cited

U.S. PATENT DOCUMENTS

| | | | | |
|---|---|---|---|---|
| 5,031,768 A * | 7/1991 | Fischer | A61B 50/33 | 206/370 |
| 6,345,747 B1 * | 2/2002 | Ogata | A45C 13/18 | 224/267 |
| 2001/0052533 A1 * | 12/2001 | Kubasik | A45F 3/04 | 224/642 |
| 2007/0221461 A1 * | 9/2007 | Carmona | A45C 13/30 | 190/101 |
| 2009/0057304 A1 * | 3/2009 | Lamarche | B65D 21/0222 | 220/4.21 |

(Continued)

*Primary Examiner* — Robert Poon

(74) *Attorney, Agent, or Firm* — Intellectual Property Consulting, LLC; Jared Rovira

(57) ABSTRACT

The present invention describes a tourniquet carrier assembly that includes a case comprising a base portion, a lid portion, at least one aperture in the case, and at least one groove operable to receive at least one corresponding tab, a tourniquet, and a band configured to receive the case and bound the lid portion to the base portion. Without the carrier strap, the base portion is configured to engage but not attach to the lid portion when each groove receives each corresponding tab, and the tab and groove connections are operable to prevent lateral displacement but allow vertical displacement of the lid portion from the base portion.

5 Claims, 10 Drawing Sheets

(56) References Cited

U.S. PATENT DOCUMENTS

| | | | | |
|---|---|---|---|---|
| 2016/0135310 | A1* | 5/2016 | Kawai | H01F 17/06<br>336/92 |
| 2016/0368669 | A1* | 12/2016 | Magana | B65D 11/20 |
| 2021/0212700 | A1* | 7/2021 | Plott | A61B 50/31 |

* cited by examiner

QUICK RELEASE TOURNIQUET CARRIER

RELATED APPLICATIONS

This application is a continuation of U.S. patent application Ser. No. 17/929,292, which itself claims priority to U.S. Provisional Application No. 63/239,527 filed Sep. 1, 2021. The entire contents of the above applications are hereby incorporated by reference as though fully set forth herein.

FIELD

The present invention relates in general to the field of tactical gear. More specifically, the present invention relates to a personal tourniquet carrier that allows for quick access.

BACKGROUND

Tourniquets are often carried on-person in tactical and survival circumstances to quickly stop or slow traumatic bleeding immediately after injury and before the injured person may receive complete medical care. Tourniquets are intended to be used either by the injured party or to aid someone else. They are typically lightweight, portable, and accessible for fast deployment. This function is critical for military, law enforcement personnel, first responders and in survival circumstances where the potential for serious injury is high and access to medical treatment is very limited.

For example, military personnel are typically provided tourniquets during times of military deployment. Such tourniquets are often strapped to the outside of a uniform or carried in a backpack. The soldier must rush to access the tourniquet as fast as possible when someone is seriously injured and begins bleeding traumatically. However, current carrying means often render the tourniquet useless because it cannot be accessed and applied fast enough to save an injured person's life. A severed limb may cause one to bleed to death in less than ten seconds, often before a tourniquet can be unstrapped or withdrawn from a backpack and then applied to the limb.

Another shortfall of a typical tourniquet is it is one more piece of equipment that a solider or enforcement officer must remember to attach to a uniform or pack in a backpack. Therefore, it may be inadvertently left behind during times of high stress and rapid combat deployment.

Current tourniquet carriers are typically made of a plate or holster which is strapped or clipped to a person's belt. The tourniquet is inserted into the holster or strapped to the plate and held fast with one or more elastic cords or straps. To remove the tourniquet, the user must remove the cords or straps and pull the tourniquet from the plate or holster. This often requires two or more steps when time is critical.

Removal of the tourniquet may be frustrated and delayed if the attachment cords are improperly attached or twisted. The attachment cords or straps may also get stuck when the user attempts to remove them. On the other hand, the cords or straps might break or detach during rigorous activity, which may cause the user to lose the tourniquet.

There will always be a need for faster deployment of a tourniquet to increase the chance of survival when severe injuries happen. Every second is critical. Accordingly, there is a need for a tourniquet carrier that incorporates a quick-release mechanism which allows the tourniquet to be deployed and ready for use in a single, fluid motion.

BRIEF SUMMARY OF THE INVENTION

The present invention is a quick-release tourniquet carrier that provides an individual with the necessary means to immediately access and deploy a tourniquet in emergency situations. The innovative design of the carrier includes a tourniquet case and an elastic compression band attached to a mounting plate which is attached to the user. The tourniquet is placed within the case, which comprises at least two separate pieces. The case is closed and then slipped into the compression band, which squeezes the case to hold it together and in the ready position. To deploy the tourniquet, the user pulls one of two ripcords attached to the ends of the tourniquet. The case breaks apart immediately as it exits the compression band, thereby allowing for immediate use of the tourniquet.

DETAILED DESCRIPTION

Figure 1:
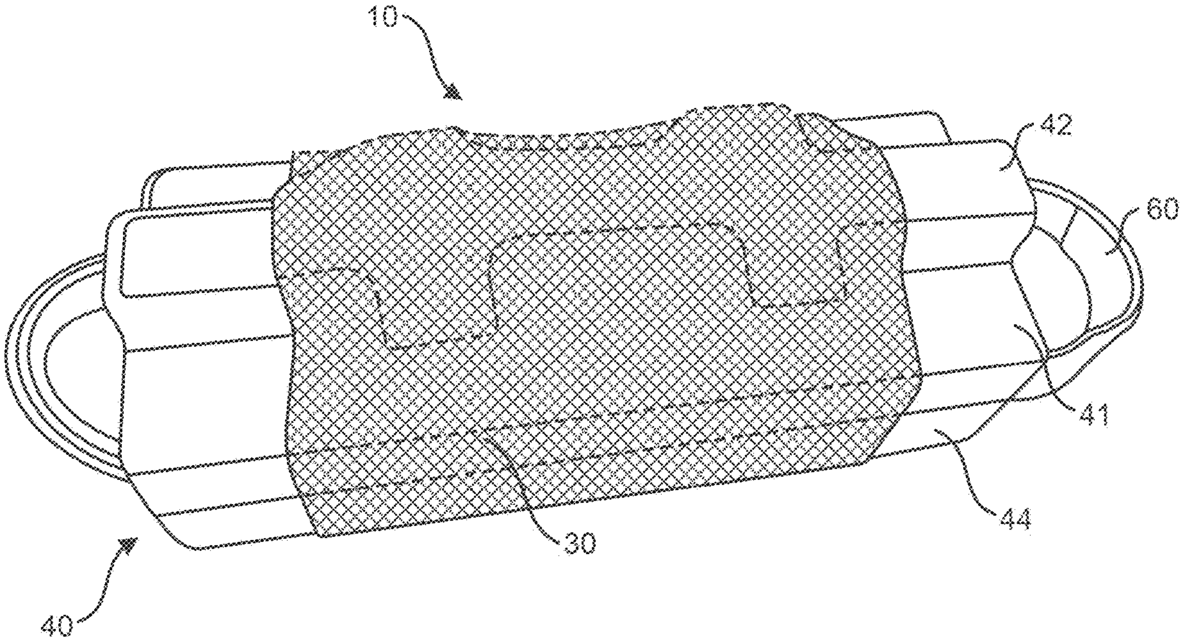
FIG. 1 is a top perspective view of the carrier showing the case within the compression band.
Figure 2:
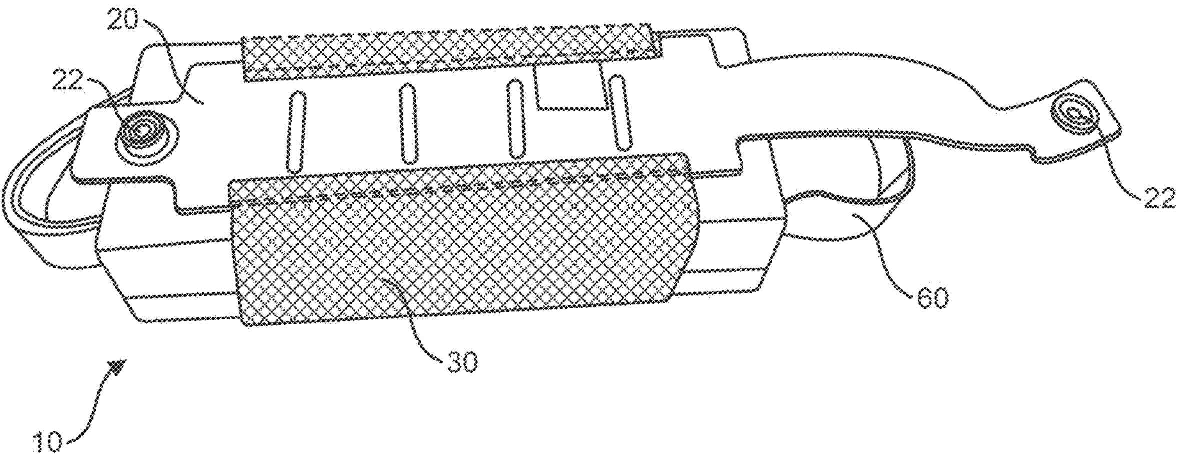
FIG. 2 is a bottom perspective view of the carrier.

The present invention includes a tourniquet carrier 10 comprising a mounting plate 20, a compression band 30, and a case 40, as shown in FIG. 1 and FIG. 2. In a preferred embodiment, the mounting plate 20 includes a strap 21 and a fastener 22, depicted in FIG. 2. Although the preferred embodiment of fastener 22 is a standard snap to secure carrier 10 to a person or other tactical gear, other types of releasable fasteners known in the prior art may be used, such as hook and loop fasteners, a button or a clip.

Figure 3:
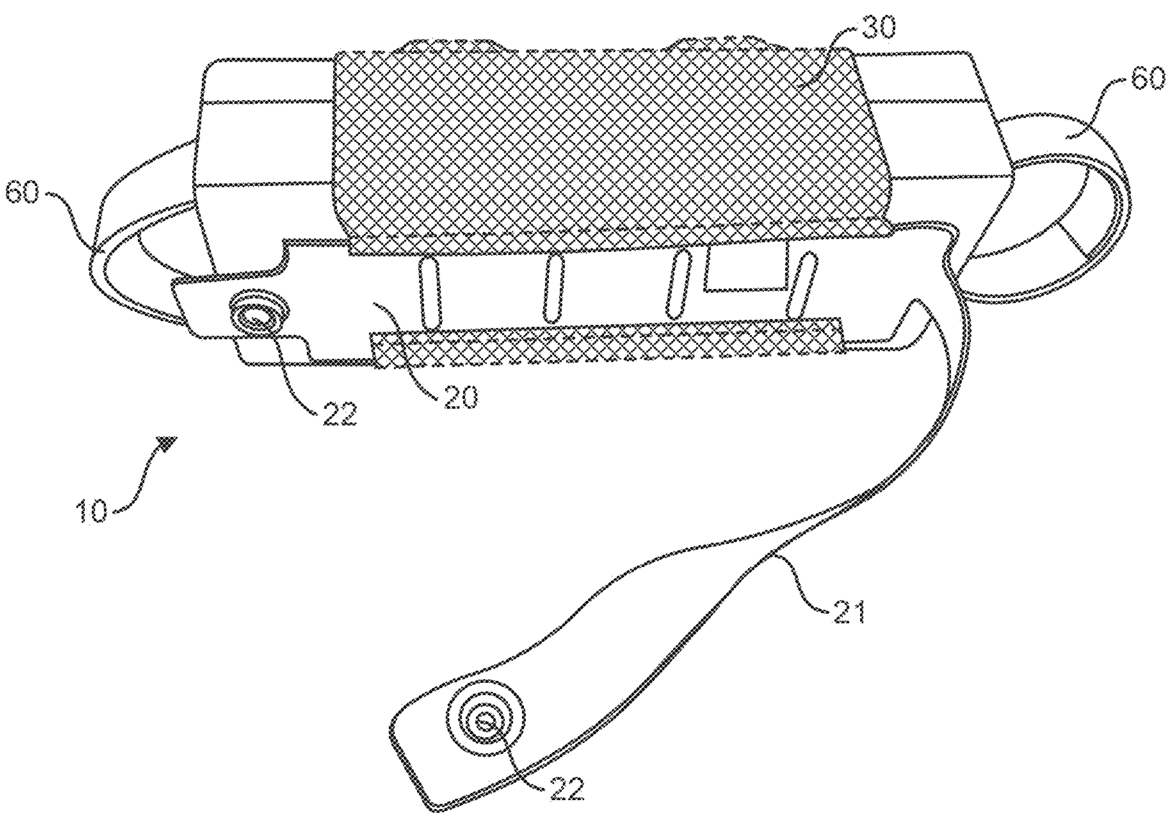
FIG. 3 is a side perspective view of the carrier.

Mounting plate 20 may be comprised of any durable material such as a lightweight plastic polymer commonly used with tactical gear. Strap 21 shown in FIG. 3 is universal and may be comprised of a durable, pliable material, and operable to attach to a belt or external gear.

Figure 6:
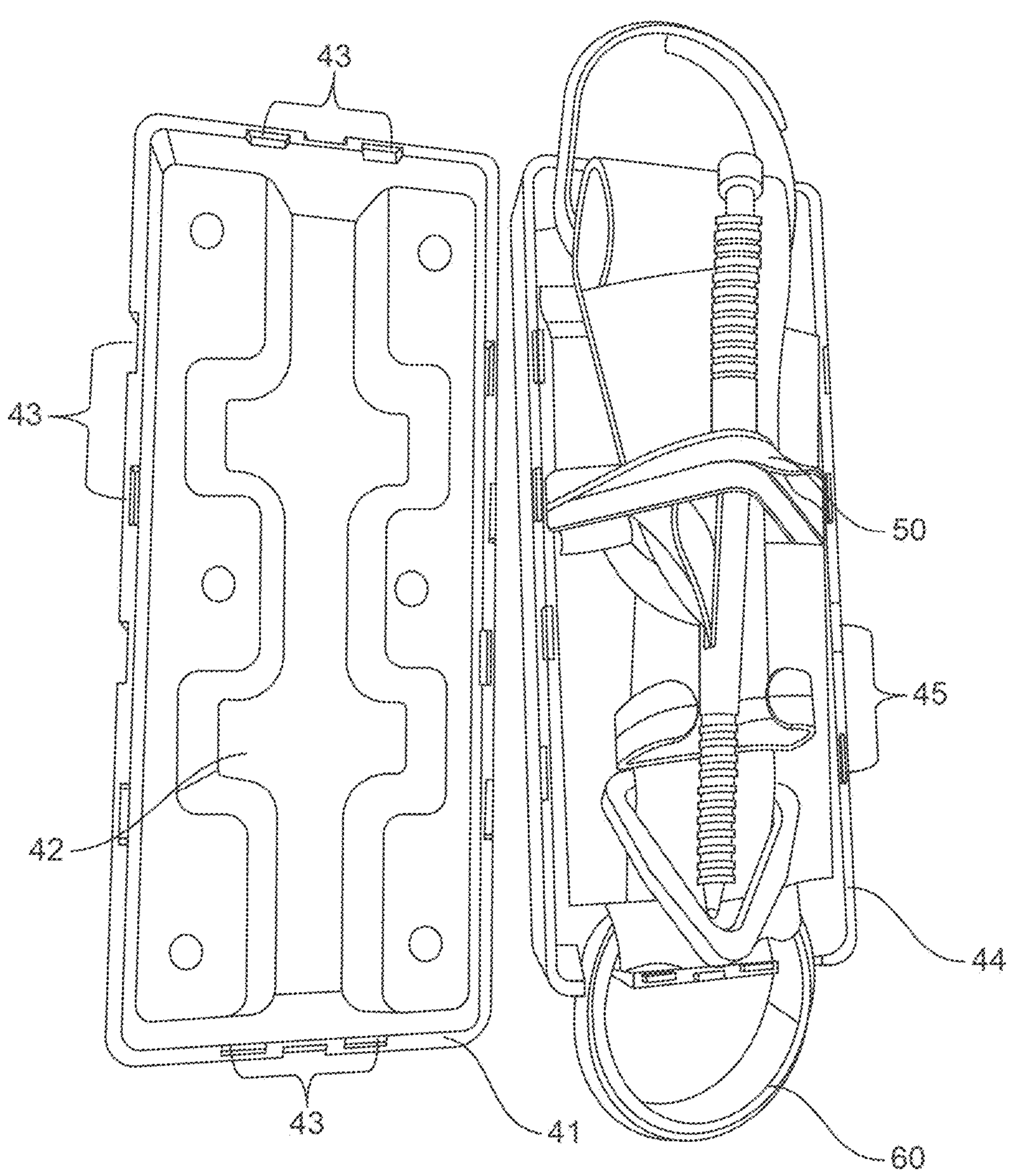
FIG. 6 is a top view of the bottom portion and the top portion of the case in the open configuration with a tourniquet placed within the bottom portion of the case.
Figure 7:
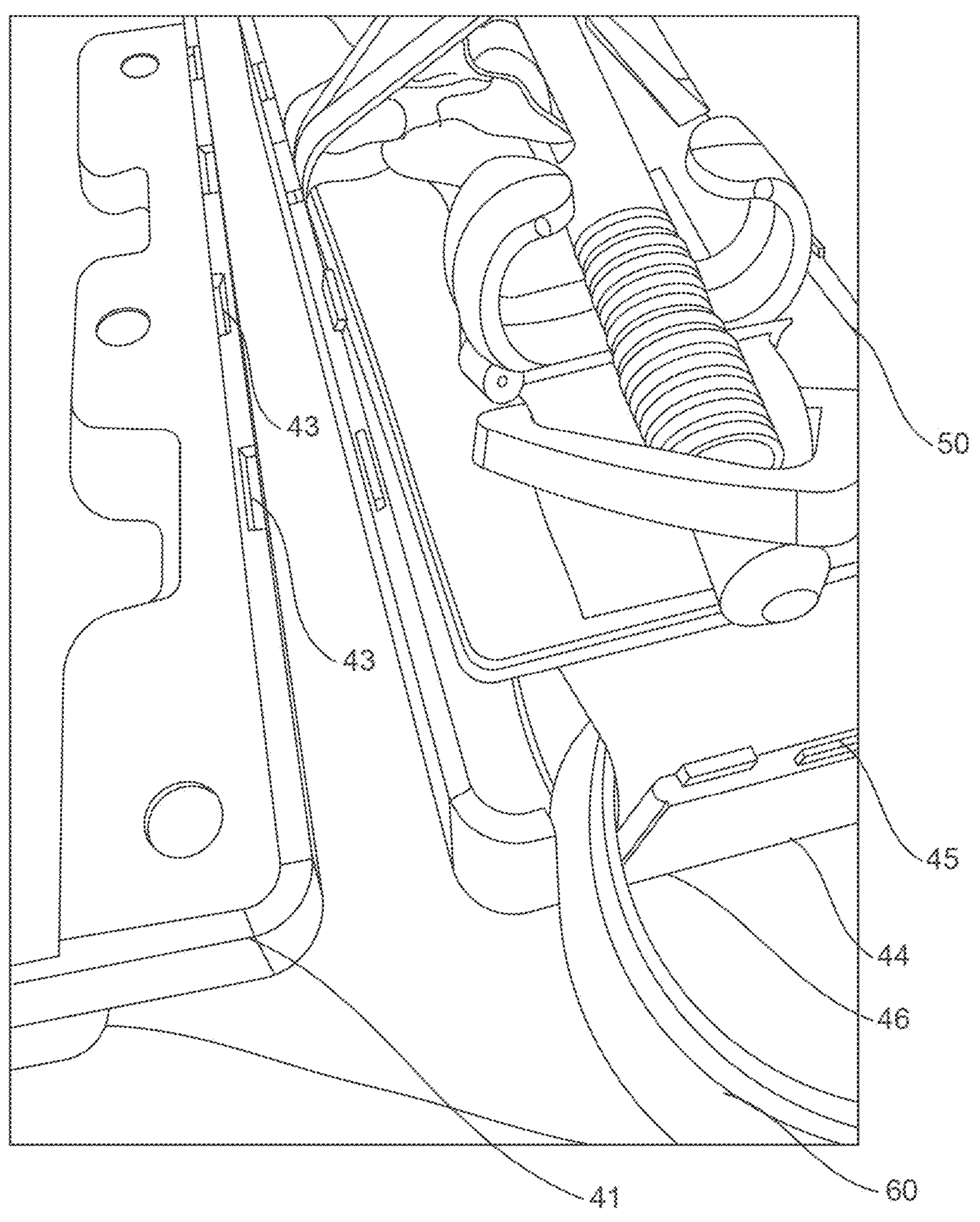
FIG. 7 is a perspective view of the bottom portion and the top portion of the case in the open configuration with a tourniquet placed within the bottom portion of the case.
Figure 8:
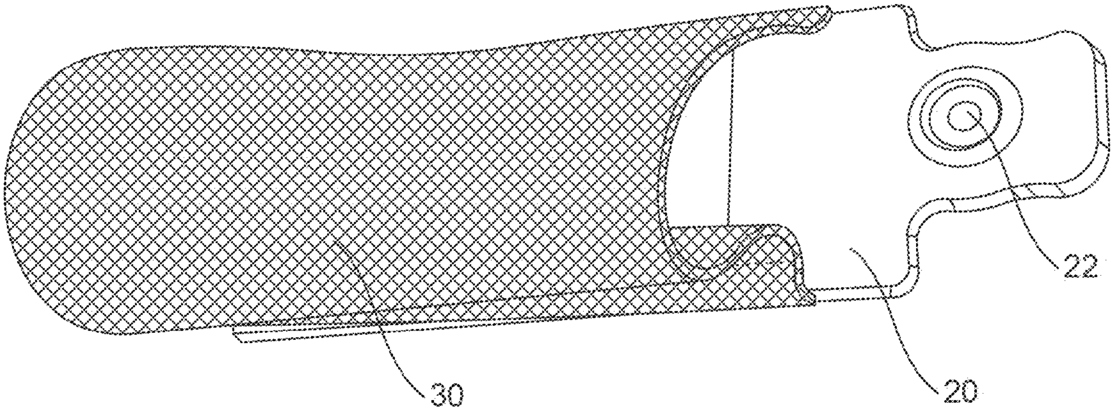
FIG. 8 is a top perspective view of the compression band attached to the mounting plate.
Figure 9:
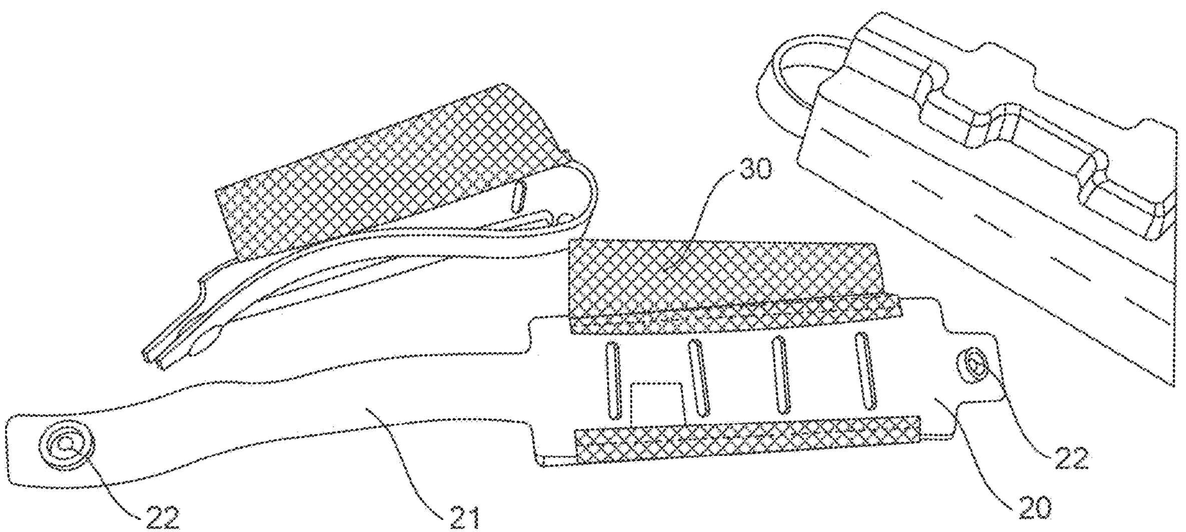
FIG. 9 is a bottom view of the mounting plate and the compression band.
Figure 10:
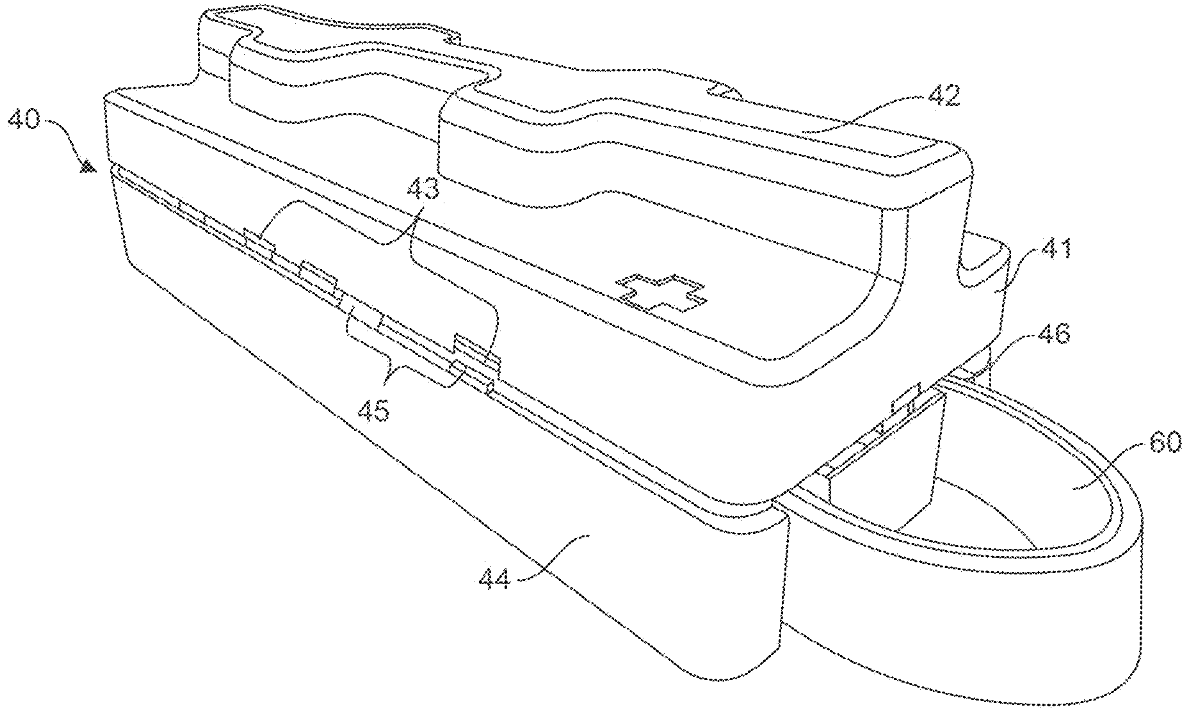
FIG. 10 is a perspective view of the case in the closed configuration with a tourniquet enclosed.

Compression band 30 is attached to mounting plate 20 by any typical means, such as stitching as shown in FIG. 2 and FIG. 9. Case 40 is hollow and is designed to house a tourniquet 50. In one embodiment, case 40 comprises lid portion 41, recessed interior cavity 42, grooves 43, base portion 44, tabs 45 and aperture openings 46, as shown in FIG. 6 and FIG. 10. A ripcord 60 is attached to each end of tourniquet 50. In the preferred embodiment, Case 40 is made from a rigid material; however, many variations in materials may allow for full operability. Although the preferred embodiment of ripcord 60 uses hook and loop fasteners. i.e. VELCRO®, to secure ripcord 60 to tourniquet 50, any other type of fastener known in the prior art may be used.

Figure 4:
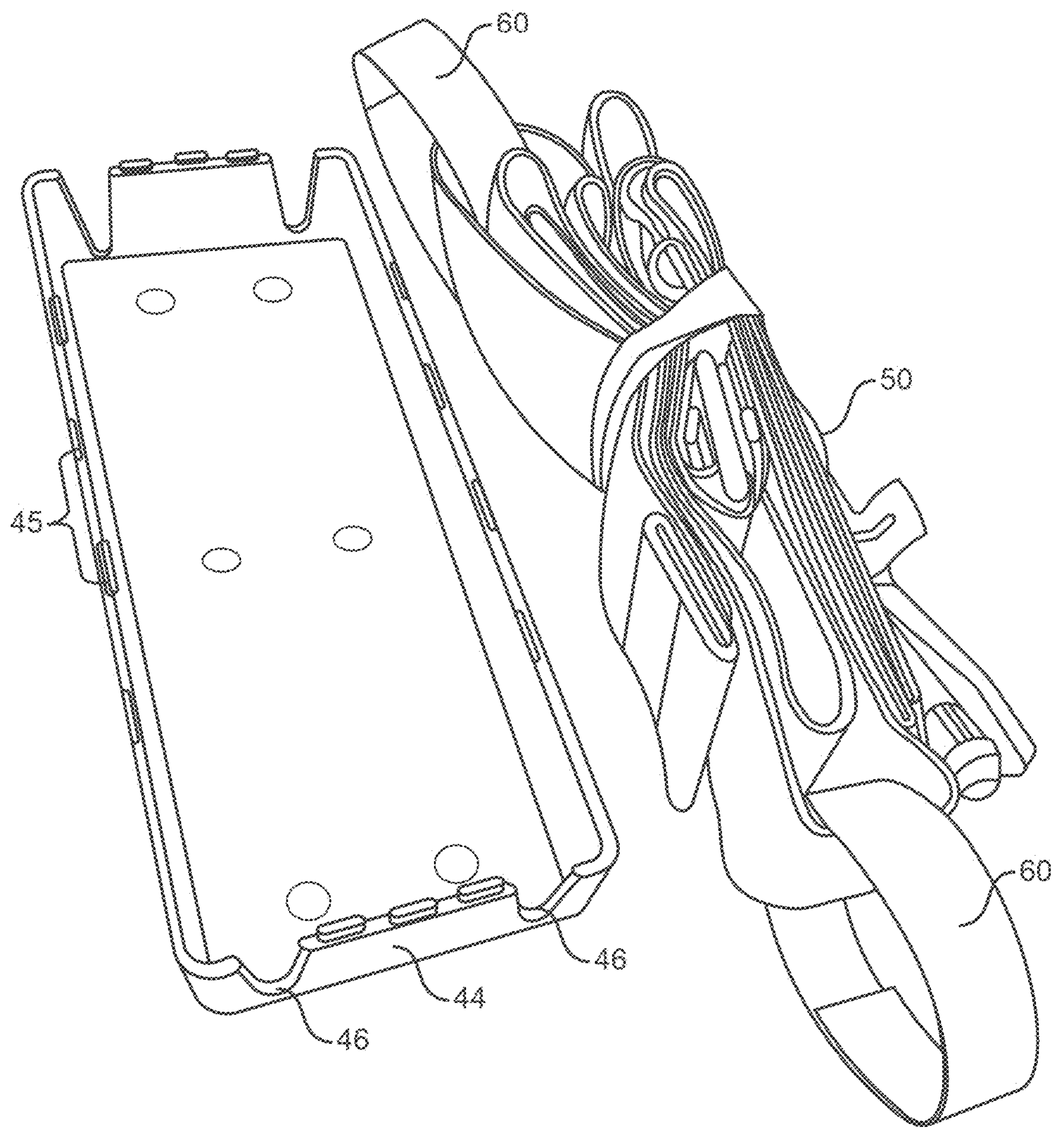
FIG. 4 is a top view of the bottom portion of the case in the open configuration with a tourniquet.
Figure 5:
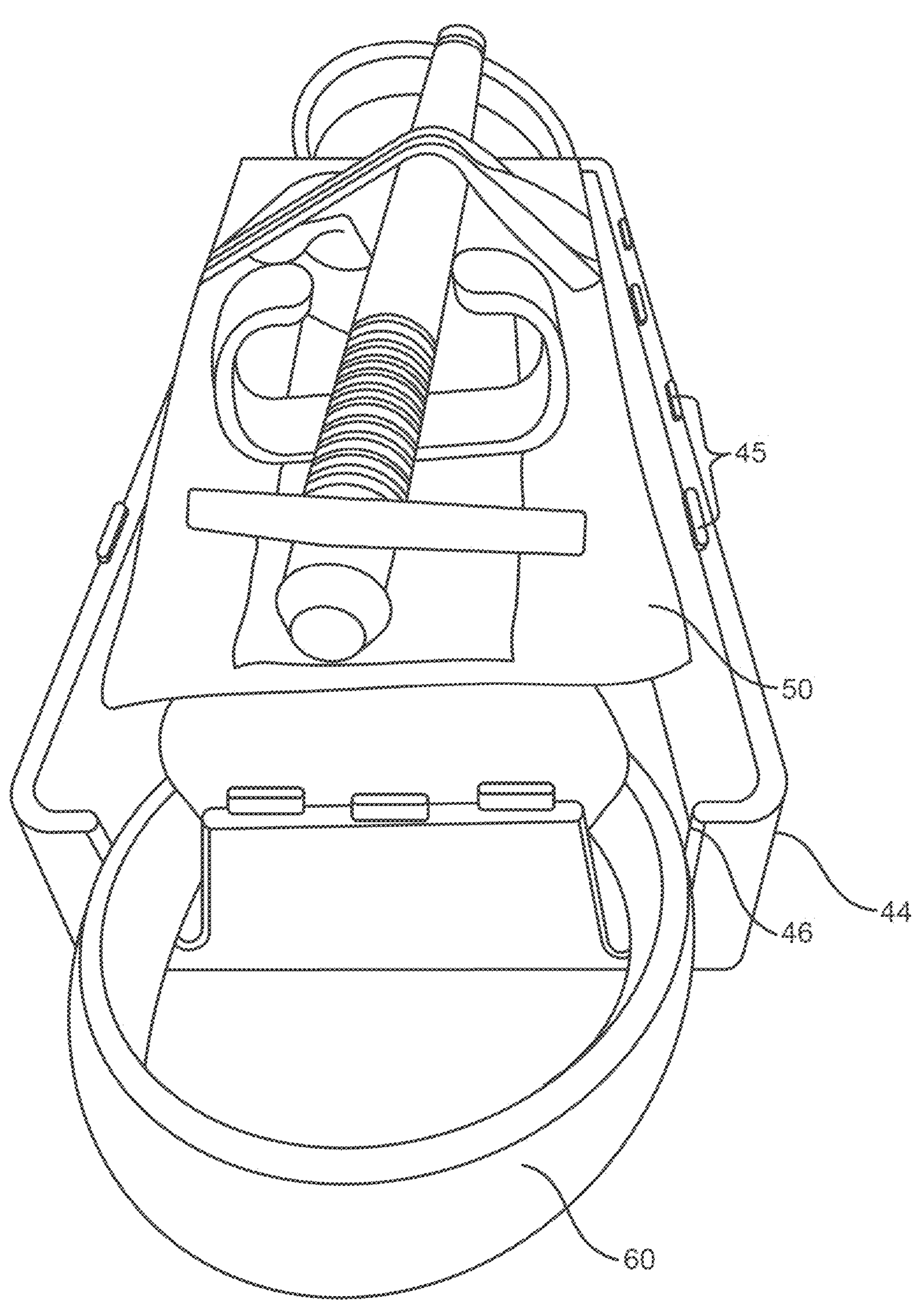
FIG. 5 is a perspective view of the bottom portion of case in the open configuration with a tourniquet placed within the bottom portion of the case.

To prepare the tourniquet for deployment, ripcords 60 are directly or indirectly coupled to tourniquet 50 on ether end as shown in FIG. 4. Tourniquet 50 is then placed in base portion 44 such that ripcords 60 extend through apertures 46 as shown in FIGS. 5-7 and FIG. 10. Lid portion 41 is then placed onto base portion 44 such that tabs 45 are aligned with and fit inside corresponding grooves 43 to form interlocking connections, which restrict lateral movement of lid portion 41 and base portion 44 thereby preventing them from sliding apart. As a result, lid portion 41 and base portion 44 are held in alignment when case 40 is inserted into compression band 30.

However, grooves 43 and tabs 45 are configured such that they do not form a perpendicular locking connection which holds lid portion 41 and base portion 44 together. Lid portion 41 and base portion 44 are not held against each other in a perpendicular direction, but they will not slide apart in a lateral direction. See FIGS. 7 and 10. Instead of grooves 43 and tabs 45, other means to create a lateral locking configuration such as offsetting partial lips of lid portion 41 and base portion 44.

In operation, tourniquet 50 is placed into base portion 44. Lid portion 41 to base portion 44 by inserting tabs 45 into grooves 43 as explained above and shown in FIG. 10. With case 40 in the closed configuration, the user places base portion 44 against mounting plate 20 and slides case 40 longitudinally along mounting plate 20 and into compression band 30, which stretches over case 40 as shown in FIG. 1. Case 40 is preferably situated such that approximately equal portions of each end protrude from compression band 30.

Compression band 30 comprises an elastic material which does not impose a substantial friction force against case 40. The absence of friction allows the user to slip case 40 into compression band 30 despite the compressive force that compressive band 30 applies to case 40. Compression band 30 may be fabricated from any typical material with elastic properties; however, a durable material such as polyester may be preferred. Compression band 30 is configured such that sufficient compressive force is applied to hold case 40 against mounting plate 20 during rigorous movement. However, it is intended that an adult person of average strength will be able to overcome the said compressive force to load and deploy case 40.

As shown in FIG. 6 and FIG. 10, a preferred embodiment of lid portion 41 comprises a recessed interior cavity 42 configured to roughly conform to the shape of a tourniquet. Recessed interior cavity 42 provides several benefits. Tourniquet 50 rests within recessed interior cavity 42 when case 40 is in the closed position. The shape of recessed interior cavity 42 creates a tight fit over tourniquet 50, which prevents movement of tourniquet 50 and eliminates rattle. Recessed interior cavity 42 also reduces the overall size of carrier 10. The shape of recessed interior cavity 42 creates a protruding, multi-planar surface over which compression band 30 fits as shown in FIG. 1. Compression band 30 stretches around and conforms to the protrusion created by recessed interior cavity 42, which and helps secure case 40 to mounting plate 20.

In a preferred embodiment, carrier 10 is removably attached to the user with strap 21 in a location which may be quickly and easily reached by hand, such as the waist. To deploy tourniquet 50, the user grips either of ripcords 60 and pulls with sufficient force to extract case 40 from the grip of compression band 30. When case 40 exits compression band 30, lid portion 41 and base portion 44 will split apart from one another due to gravitational force, thereby freeing tourniquet 50 for immediate use. The time needed to access tourniquet 50 is reduced compared with other tourniquet carriers known in the art, which typically require the user to fumble with multiple elastic cords or straps which are subject to snagging or slippage when pulled upon.

For the purposes of promoting an understanding of the principles of the invention, reference has been made to the preferred embodiments illustrated in the drawings, and specific language has been used to describe these embodiments. However, this specific language intends no limitation of the scope of the invention, and the invention should be construed to encompass all embodiments that would normally occur to one of ordinary skill in the art. The particular implementations shown and described herein are illustrative examples of the invention and are not intended to otherwise limit the scope of the invention in any way. For the sake of brevity, conventional aspects of the device (and components of the individual operating components of the system) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

What is claimed is:

1. A tourniquet carrier assembly comprising:

a case comprising a base portion, a lid portion, and at least one aperture in the case, the lid portion defined by a top surface and a sidewall extending around a perimeter of the top surface, the base portion defined by a bottom surface with a sidewall extending around the perimeter of the bottom surface, wherein, the sidewall of the lid portion is configured to sit on top of the sidewall of the base portion, wherein, the lid portion is completely detachable from the base portion, the sidewall of the base portion further comprises one or more tabs extending in a vertical direction away from the bottom surface, the sidewall of the top portion comprises one or more grooves vertically recessed into the side wall, and wherein, each of the one or more grooves is aligned to receive each of the one or more tabs such that each tab is fully encased within each corresponding groove when the case is in a closed position, a tourniquet, and a band configured to receive the case, wherein the band is operable to hold the base portion and lid portion together, and wherein the case is operable to encase the tourniquet.

2. The tourniquet carrier assembly of claim 1 further comprising a mounting plate attached to the band.

3. The tourniquet carrier assembly of claim 1 comprising a rip cord configured to attach to the tourniquet within the carrier, wherein a portion of the rip cord extends through at least one aperture opening and is accessible from an exterior of the case.

4. The tourniquet carrier assembly of claim 1 wherein either the base portion or the lid portion comprise a recessed interior cavity configured to conform to the shape of the tourniquet.

5. The tourniquet carrier assembly of claim 2 further comprising a strap connected to the mounting plate.

* * * * *